United States Patent
Stokbroekx et al.

[11] Patent Number: 5,985,878
[45] Date of Patent: Nov. 16, 1999

[54] ANGIOGENESIS INHIBITING PYRIDAZINAMINES

[75] Inventors: Raymond Antoine Stokbroekx, Beerse; Marcel Jozef Maria Van der Aa, Turnhout; Marc Willems, Vosselaar; Lieven Meerpoel, Merksplas; Marcel Gerebernus Maria Luyckx, Geel, all of Belgium; Robert Tuman, Spring House, Pa.

[73] Assignee: Janssen Pharmaceuticals, N.V., Beerse, Belgium

[21] Appl. No.: 09/119,075

[22] Filed: Jul. 9, 1998

[30] Foreign Application Priority Data

Jan. 15, 1996 [EP] European Pat. Off. ............ 96.200.085

[51] Int. Cl.⁶ .......................... A61K 31/50; A61K 31/55; C07D 417/14
[52] U.S. Cl. .......................... 514/252; 514/183; 514/212; 514/218; 514/248; 540/470; 540/481; 540/553; 540/575; 544/237; 544/238
[58] Field of Search .................. 514/252; 544/238

[56] References Cited

U.S. PATENT DOCUMENTS

| | | | |
|---|---|---|---|
| 4,992,433 | 2/1991 | Stokbroekx et al. | 514/252 X |
| 5,001,125 | 3/1991 | Stokbroekx et al. | 514/252 |
| 5,100,893 | 3/1992 | Stokbroekx et al. | 514/252 |
| 5,112,825 | 5/1992 | Stokbroekx et al. | 514/253 |
| 5,196,535 | 3/1993 | Stokbroekx et al. | 546/209 |
| 5,242,924 | 9/1993 | Diana | 514/252 |
| 5,461,053 | 10/1995 | Boigegrain et al. | 514/247 |

FOREIGN PATENT DOCUMENTS 0 429 344  11/1990  European Pat. Off. .

*Primary Examiner*—Michael G. Ambrose
*Attorney, Agent, or Firm*—Ellen Ciambrone Coletti

[57] ABSTRACT

This invention concerns compounds of formula

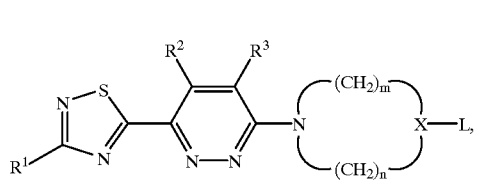

(I)

the N-oxide forms, the pharmaceutically acceptable acid addition salts and stereochemically isomeric forms thereof, wherein X is CH or N; m is 2 or 3 and n is 1, 2 or 3; wherein 1 or 2 C-atoms of the $CH_2$ groups of the

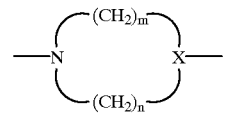

moiety which may also contain one double bond, may be substituted with $C_{1-6}$alkyl, amino, aminocarbonyl, mono- or di($C_{1-6}$alkyl)amino, $C_{1-6}$alkyloxycarbony, $C_{1-6}$alkylcarbonylamino, hydroxy or $C_{1-6}$alkyloxy; and/or 2 C-atoms of said $CH_2$ groups may be bridged with $C_{2-4}$alkanediyl; $R^1$ is hydrogen, $C_{1-6}$alkyl, $C_{1-6}$alkyloxy, $C_{1-6}$alkylthio, amino, mono- or di($C_{1-6}$alkyl)amino, Ar, ArNH—, $C_{3-6}$cycloalkyl, hydroxymethyl or benzyloxymethyl; $R^2$ and $R^3$ are hydrogen, or taken together may form a bivalent radical of formula —CH=CH—CH=CH—; in case X represents CH then L is a radical $L^1$, $L^2$ or $L^3$; or in case X represents N then L is a radical $L^2$ or $L^3$; $L^1$ is Ar-$C_{1-6}$alkyloxy, Ar-oxy, Ar-thio, Ar-carbonylamino, di-Ar-methyloxy-, N-Ar-piperazinyl, N-Ar-homopiperazinyl, 2-benzimidazolinonyl, Ar—$NR^4$—, Ar-Alk-$NR^4$—, Ar—$NR^4$-Alk-$NR^5$— or Het-$NR^4$—; $L^2$ is Ar, Ar-carbonyl, Ar—CH=CH—$CH_2$—, naphtalenyl or Het; $L^3$ is $C_{1-6}$alkyl substituted with one or two radicals selected from Ar, Ar-oxy, or Ar-thio, further optionally substituted with cyano or hydroxy; 2,2-dimethyl-1,2,3,4-tetrahydro-naphtalenyl; 2,2-dimethyl-1H-2,3-dihydroindenyl;Ar-piperidinyl or Ar—$NR^4$-Alk-; $R^4$ and $R^5$ are each independently selected from hydrogen or $C_{1-6}$alkyl; Alk is $C_{1-6}$alkanediyl; their preparation, compositions containing them and their use as a medicine.

10 Claims, No Drawings

ANGIOGENESIS INHIBITING PYRIDAZINAMINES

CROSS-REFERENCE TO RELATED APPLICATIONS

This application is the national stage of application No. PCT/EP97/00201, filed on Jan. 14, 1997, which application claims priority from EP 96.200.085.7, filed on Jan. 15, 1996.

This invention concerns 3-(3-substituted-1,2,4-thiadiazol-5-yl)pyridazinamines acting as angiogenesis inhibitors, and their preparation; it further relates to compositions comprising them, as well as their use as a medicine.

Angiogenesis, i.e. the formation of new vessels by endothelial cells, plays an important role in a variety of physiologic and pathophysiologic processes. The development of a vascular supply is essential for the growth, maturation and maintenance of normal tissues. It is also required for wound healing. However angiogenesis is also critical for solid tumor growth and metastasis and is involved in a variety of other pathological conditions such as neovascular glaucoma, diabetic retinopathy, psoriasis and rheumatoid arthritis. These pathological states are characterized by augmented angiogenesis during which normally quiescent endothelial cells become activated, degrade extracellular matrix barriers, proliferate, and migrate to form new vessels. To control these angiogenesis dependent disorders, compounds with angiogenesis inhibitory properties would be very useful.

Several compounds inhibiting angiogenesis, also called angiostatics, angio-inhibitors or angiogenic antagonists, are disclosed in the art. For instance hydrocortisone is a well known angiogenesis inhibitor (Folkman et al., Science 230:1375, 1985' "A new class of steroids inhibits angiogenesis in the presence of heparin or a heparin fragment"; Folkman et al., Science 221:719, 1983, "Angiogenesis inhibition and tumor regression caused by heparin or a heparin fragment in the presence of cortisone").

In EP-0,435,381-A1, published on Jul. 3 1991, pyridazinamines are described having antipicornaviral activity. The compounds of the present invention differ from the cited pyridazinamines by the fact that they are invariably substituted with a thiadiazolyl moiety and particularly by the fact that unexpectedly these compounds have angiogenesis inhibiting properties.

This invention concerns compounds of formula

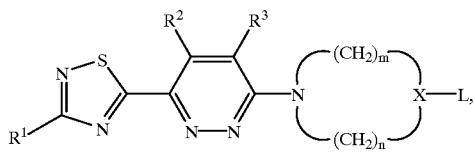

(I)

the N-oxide forms, the pharmaceutically acceptable acid addition salts and stereochemically isomeric forms thereof, wherein X is CH or N; m is 2 or 3 and n is 1, 2 or 3; wherein 1 or 2 C-atoms of the $CH_2$ groups of the

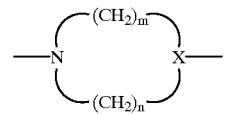

moiety, which may also contain one double bond, may be substituted with $C_{1-6}$alkyl, amino, aminocarbonyl, mono- or di($C_{1-6}$alkyl)amino, $C_{1-6}$alkyloxycarbonyl, $C_{1-6}$alkylcarbonylamino, hydroxy or $C_{1-6}$alkyloxy;

and/or 2 C-atoms of said $CH_2$ groups may be bridged with $C_{2-4}$alkanediyl;

$R^1$ is hydrogen, $C_{1-6}$alkyl, $C_{1-6}$alkyloxy, $C_{1-6}$alkylthio, amino, mono- or di($C_{1-6}$alkyl)amino, Ar, ArNH—, $C_{3-6}$cycloalkyl, hydroxymethyl or benzyloxymethyl;

$R^2$ and $R^3$ are hydrogen, or taken together may form a bivalent radical of formula

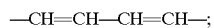—CH=CH—CH=CH—;

in case X represents CH then L is a radical $L^1$, $L^2$ or $L^3$; or in case X represents N then L is a radical $L^2$ or $L^3$;

$L^1$ is Ar-$C_{1-6}$alkyloxy, Ar-oxy, Ar-thio, Ar-carbonylamino, di-Ar-methyloxy-, N-Ar-piperazinyl, N-Ar-homopiperazinyl, 2-benzimidazolinonyl, Ar—$NR^4$—, Ar-Alk-$NR^4$—, Ar—$NR^4$-Alk-$NR^5$— or Het-$NR^4$—;

$L^2$ is Ar, Ar-carbonyl, Ar—CH=CH—$CH_2$—, naphtalenyl or Het;

$L^3$ is $C_{1-6}$alkyl substituted with one or two radicals selected from Ar, Ar-oxy, or Ar-thio, further optionally substituted with cyano or hydroxy; 2,2-dimethyl-1,2,3,4-tetrahydro-naphtalenyl; 2,2-dimethyl-1H-2,3-dihydroindenyl; Ar-piperidinyl or Ar—$NR^4$-Alk-;

$R^4$ and $R^5$ are each independently selected from hydrogen or $C_{1-6}$alkyl; each Ar is independently selected from phenyl; phenyl substituted with 1, 2 or 3 substituents each independently selected from halo, amino, nitro, $C_{1-6}$alkyl, trihalomethyl, $C_{1-6}$alkyloxy, $C_{1-6}$alkyloxycarbonyl or hydroxy; phenyl substituted with an oxadiazole substituted with $C_{1-6}$alkyl;

Het is a monocyclic or bicyclic heterocycle; monocyclic heterocycles are pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; bicyclic heterocycles are indolyl, quinolinyl, quinazolinyl, quinoxalinyl, benzoxazolyl, benzisoxazolyl, benzothiazolyl, benzisothiazolyl, benzofuranyl, benzothienyl, benzopyranyl, benzothiopyranyl and thiochromanyl; each monocyclic and bicyclic heterocycle may optionally be substituted on a carbon atom by 1 or 2 substituents each independently selected from halo, $C_{1-4}$alkyl, $C_{1-4}$alkyloxy, or trihalomethyl; and Alk is $C_{1-6}$alkanediyl.

The heterocycles in the definition of Het are preferably connected to the rest of the molecule by a carbon atom. 2-Benzimidazolinonyl is preferably connected to the rest of the molecule by a nitrogen atom.

In N-Ar-piperazinyl and N-Ar-homopiperazinyl, the Ar group is situated on the nitrogen atom of the piperazinyl or homopiperazinyl moiety.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 to 6 carbon atoms such as, for example, pentyl, 2-methylbutyl, hexyl, 2-methylpentyl and the like; $C_{2-4}$alkanediyl defines bivalent straight and branched chain saturated hydrocarbon radicals having from 2 to 4 carbon atoms such as, for example, 1,2-ethanediyl, 1,3-propanediyl, 1,4-butanediyl and the like; $C_{1-6}$alkanediyl defines bivalent straight and branched chain saturated hydrocarbon radicals having from 1 to 6 carbon atoms such as, for example, methylene, 1,2-ethanediyl, 1,3-propanediyl, 1,4-butanediyl, 1,5-pentanediyl, 1,6-hexanediyl and the like. $C_{3-6}$cycloalkyl comprises cyclopropyl, cyclobutyl, cyclopentyl and cyclohexyl.

Examples of the

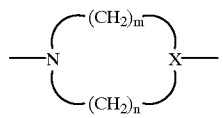

moiety are

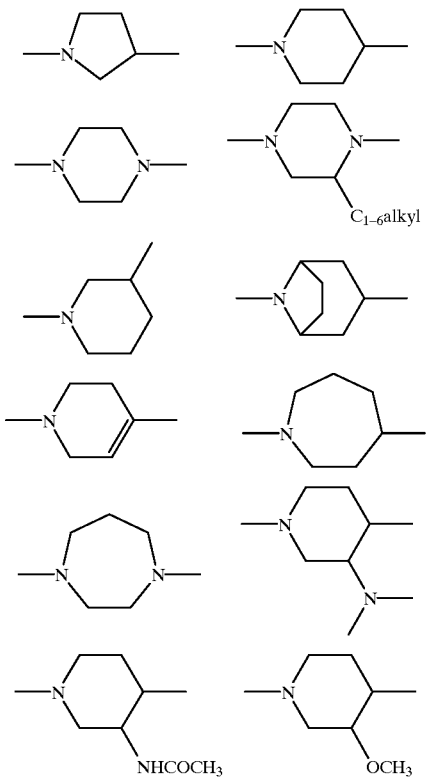

The pharmaceutically acceptable acid addition salts as mentioned hereinabove are meant to comprise the therapeutically active non-toxic acid addition salt forms which the compounds of formula (I) are able to form. Said salts can conveniently be obtained by treating the base form of the compounds of formula (I) with appropriate acids such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term acid addition salt as used hereinabove also comprises the solvates which the compounds of formula (I) as well as the salts thereof, are able to form. Such solvates are for example hydrates, alcoholates and the like.

The term "stereochemically isomeric forms" as used hereinbefore defines all the possible isomeric as well as conformational forms which the compounds of formula (I) may possess. Unless otherwise mentioned or indicated, the chemical designation of compounds denotes the mixture, more in particular the racemic mixture, of all possible stereochemically isomeric forms, said mixtures containing all diastereomers and/or enantiomers of the basic molecular structure. More in particular, stereogenic centers may have the R- or S-configuration; substituents on bivalent cyclic saturated radicals may have either the cis- or trans-configuration. For the compounds having two stereogenic centers, the relative stereodescriptors R* and S* are used in accordance with the Chemical Abstracts rules (Chemical Substance Name Selection Manual (CA), 1982 Edition, Vol. III, Chapter 20). All stereochemically isomeric forms of the compounds of formula (I) both in pure form or mixtures thereof are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Whenever used hereinafter, the term "compounds of formula (I)" is meant to also include their N-oxide forms, their pharmaceutically acceptable acid addition salts, and their stereochemically isomeric forms.

An interesting group of compounds consists of those compounds of formula (I) wherein X is CH or N, and the $CH_2$ groups of the

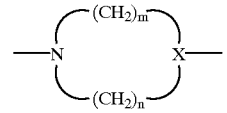

moiety are unsubstituted.

Another group of interesting compounds consists of those compounds of formula (I) wherein $R^1$ is $C_{1-6}$alkyl, X is CH and m is 2 and n is 2.

Still another group of interesting compounds consists of those compounds of formula (I) wherein $R^1$ is $C_{1-6}$alkyl, X is N and m is 2 and n is 2.

A particular group of compounds are those compounds of formula (I) wherein $R^1$ is hydrogen or di($C_{1-6}$alkyl)amino.

Preferred compounds are those compounds of formula (I) wherein $R^1$ is methyl, $R^2$ and $R^3$ are hydrogen, X is CH or N and L is Ar-piperidinyl or a phenyl substituted with 1, 2 or 3 substituents each independently selected from halo or trifluoromethyl.

More particular compounds are those compounds of formula (I) wherein $R^1$ is hydrogen or di($C_{1-6}$alkyl)amino, $R^2$ and $R^3$ are hydrogen, X is CH or N, m is 2, n is 2.

Most preferred are
3-[4-(3-chlorophenyl)-1-piperazinyl]-6-(3-methyl-1,2,4-thiadiazol-5-yl)pyridazine, or
3-(3-methyl-1,2,4-thiadiazol-5-yl)-6-[4-[3-(trifluoromethyl)phenyl]-1-piperazinyl]pyridazine,
3-(3-methyl-1,2,4-thiadiazol-5-yl)-6-[4-[3-(trifluoromethyl)phenyl]-1-piperidinyl]pyridazine,
3-(3-methyl-1,2,4-thiadiazol-5-yl)-6-[4-[4-[3-(trifluoromethyl)phenyl]-1-piperazinyl]-1-piperidinyl]pyridazine,
3-(1,2,4-thiadiazol-5-yl)-6-[4-[3-(trifluoromethyl)phenyl]-1-piperazinyl]pyridazine,
1-[6-(3-methyl-1,2,4-thiadiazol-5-yl)-3-pyridazinyl]-N-[3-(trifluoromethyl)phenyl]-4-piperidinamine, and
N,N-dimethyl-5-[6-[4-[3-(trifluoromethyl)phenyl]-1-piperazinyl]-3-pyridazinyl]-1,2,4-thiadiazol-3-amine, and
the pharmaceutically acceptable acid addition salts, the stereoisomeric forms, or the N-oxides thereof.

The compounds of the present invention can generally be prepared by reacting a pyridazine of formula (II) with an amine of formula (III), following art-known N-alkylation procedures.

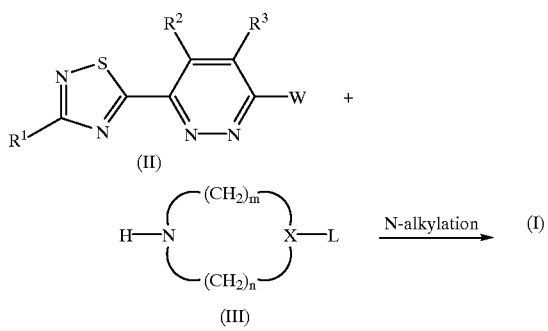

In the foregoing and following reaction schemes W represents an appropriate reactive leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. Said reaction is performed following art-known procedures such as for instance stirring and heating both reactants together in a reaction-inert solvent, e.g. dimethylformamide, preferably in the presence of a base, e.g. sodiumcarbonate. Alternatively, said N-alkylation reaction may be carried out by applying art-known conditions of phase transfer catalysis reactions. Said conditions comprise stirring the reactants, with an appropriate base and optionally under an inert atmosphere such as, for example, oxygen-free argon or nitrogen gas, in the presence of a suitable phase transfer catalyst such as, for example, a trialkylphenylmethylammonium, tetraalkylammonium, tetraalkylphosphonium, tetraarylphosphonium halide, hydroxide and the like catalysts. Somewhat elevated temperatures may be appropriate to enhance the rate of the reaction.

The compounds of formula (I) wherein X is N and L is $L^3$, said compounds being represented by formula (I-a) can also be prepared by N-alkylating a substituted piperazine of formula (IV) with a intermediate of formula (V), following similar procedures as described hereinbefore for the preparation of (I) starting from (II) and (III).

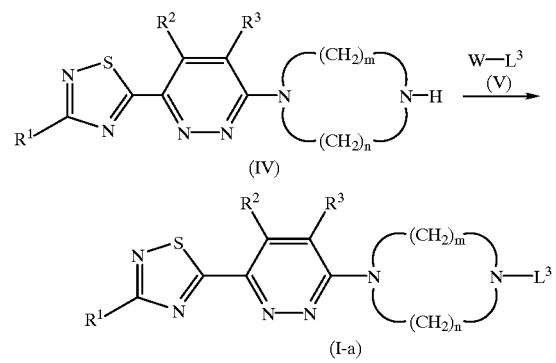

The compounds of formula (I-a) can also be prepared by reductively N-alkylating a substituted piperazine of formula (IV) with a ketone or aldehyde of formula (VI), wherein $O=L^3$ represents a derivative of formula $H—L^3$ wherein two geminal hydrogen atoms are replaced by oxygen, following art-known reductive N-alkylation procedures.

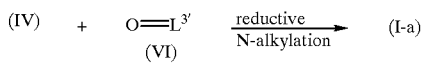

Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

The compounds of formula (I) wherein L is Ar—O-$C_{1-6}$alkyl-, said compounds being represented by formula (I-b), may also be prepared by condensing a phenol of formula (VIII) and an intermediate of formula (VII), e.g. by using the Mitsunobu reaction (Synthesis, 1, 1981).

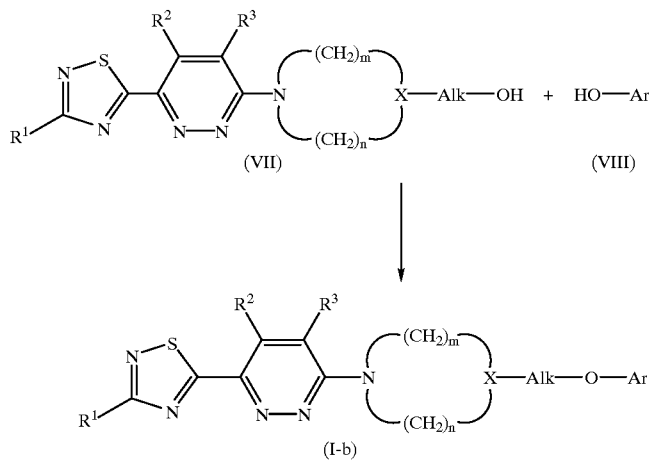

Further, the compounds of formula (I-b) can also be prepared following art-known O-alkylation reactions by alkylating a phenol of formula (VIII) with a pyridazinamine derivative of formula (IX).

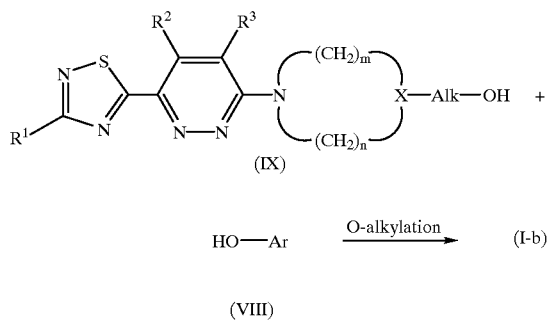

Said O-alkylation reaction can conveniently be carried out by mixing the reactants, optionally in a reaction-inert solvent such as, for example, water; an aromatic solvent, e.g. benzene, methylbenzene and the like; a $C_{1-6}$alkanol, e.g. methanol, ethanol and the like; a ketone, e.g. 2-propanone, 4-methyl-2-pentanone and the like; an ester, e.g. ethylacetate, γ-butyrolactone and the like; an ether, e.g. diethyl ether, tetrahydrofuran, 1,4-dioxane and the like; a dipolar aprotic solvent, e.g. N,N-dimethylformamide, N,N-dimethylacetamide, dimethylsulfoxide and the like; or a mixture of such solvents. The addition of an appropriate base such as, e.g. sodium carbonate, sodium hydrogen carbonate, sodium hydroxide and the like, or an organic base such as, for example, a tertiary amine, e.g. N,N-diethylethanamine, N-ethyl-N-(1-methyl ethyl)-2-propanamine and the like, may optionally be used to pick up the acid which is formed during the course of the reaction. Further, it may be advantageous to convert the phenol of formula (VIII) first into a suitable salt form thereof such as, for example, an alkali or earth alkaline metal salt, by reacting (VIII) with an appropriate base as defined hereinabove and subsequently using said salt form in the reaction with the alkylating reagent of formula (IX). Stirring and somewhat elevated temperatures may enhance the rate of the reaction; more in particular the reaction may be conducted at the reflux temperature of the reaction mixture. Additionally, it may be advantageous to conduct said alkylation reaction under an inert atmosphere such as, for example, oxygen-free argon or nitrogen gas.

Alternatively, said O-alkylation reaction may be carried out by applying art-known conditions of phase transfer catalysis reactions as described hereinbefore.

Compounds of formula (I) wherein X is CH and L is $L^3$, said compounds being represented by formula (I-c), may also be prepared by reacting a ketone (X) with an ylide of formula (XI) in a reaction-inert solvent, following art-known Wittig reaction procedures ($R^6$ and $R^7$ are aryl or $C_{1-6}$alkyl) or Homer-Emmons reaction procedures ($R^6$ is alkyloxy and $R^7$ is $O^-$). Formula (XI), $(R^6)_2$ $R^7P=L^{3'}$, represents a derivative of formula $H-L^3$ wherein two geininal hydrogen atoms are replaced by $(R^6)_2$ $R^7P=$. Appropriate solvents are, for example, hydrocarbons, e.g. hexane, heptane, cyclohexane and the like; ethers, e.g. diethyl ether, tetrahydrofuran, 1,2-dimethoxyethane and the like; dipolar aprotic solvents, e.g. dimethylsulfoxide, hexamethyl-phosphor triamide, and the like. Then the unsaturated intermediates (XII) can be reduced following an appropriate reduction procedure, for example, by stirring and, if desired, heating the unsaturated intermediates in a suitable reaction-inert solvent in the presence in the presence of a reducing agent such as, for example, a borohydride, e.g. sodium borohydride, sodium cyanoborohydride or triacetoxy borohydride. Suitable solvents are alkanols, e.g. methanol, ethanol and the like, and carboxylic acids, e.g. acetic acid and the like.

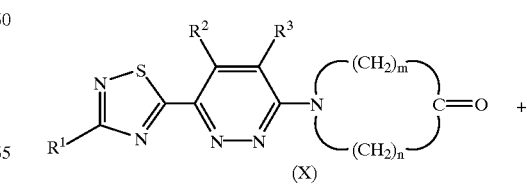

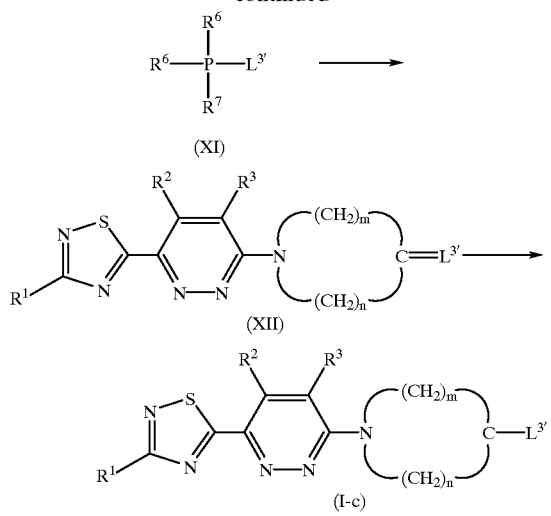

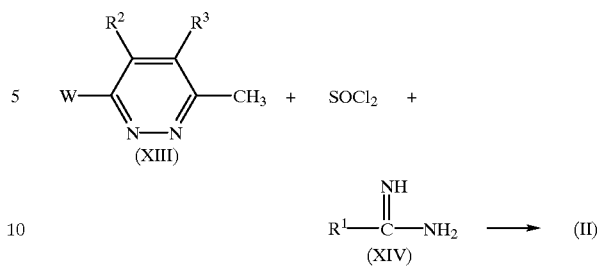

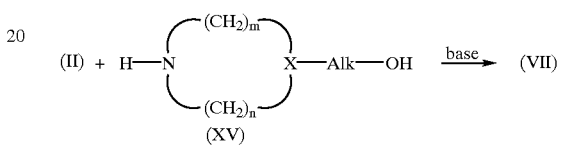

The intermediate ylides of formulae (XI) can be obtained by treating a phosphonium salt or a phosphonate with an appropriate base such as, for example, potassium tert-butoxide, methyllithium, butyllithium, sodium amide, sodium hydride, sodium alkoxide and the like bases under an inert atmosphere and in a reaction-inert solvent such as, for example, an ether, e.g. tetrahydrofuran, 1,4-dioxane and the like.

The compounds of formula (I) may further be prepared by converting compounds of formula (I) into each other according to art-known group transformation reactions. For instance, compounds of formula (I) bearing a phenyl moiety may be submitted to a bromination reaction with N-bromosuccinimide in a reaction-inert solvent to introduce a bromine atom on the phenyl moiety. Also, compounds of formula (I) may be hydrolysed under acidic conditions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. Some intermediates of formula (III) have been described in EP-0,435,381-A1.

Intermediates of formula (II) may be prepared by reacting compounds of formula (XIII), wherein W is an appropriate leaving group as defined above, with an intermediate of formula (XIV), optionally added as its acid addition salt.

Also, intermediates of formula (VII) may be prepared in an analogous way as compounds of formula (I) by reacting an intermediate of formula (II), wherein W is appropriate leaving group as defined above, with an intermediate of formula (XV), in a reaction-inert solvent, e.g. dimethylformamide, preferably in the presence of a base, e.g. sodiumcarbonate.

Compounds of formula (I) and some of the intermediates may have one or more stereogenic centers in their structure, present in a R or a S configuration.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they inhibit angiogenesis, both in vivo and in vitro.

In view of their pharmacological activity, the compounds of formula (I), their pharmaceutically acceptable acid addition salts, stereochemically isomeric forms, or N-oxide forms thereof, are inhibitors of angiogenesis. Therefore, angiogenesis inhibitors are useful to control or treat angiogenesis dependent disorders such as, e.g. ocular neovascular diseases, neovascular glaucoma, diabetic retinopathy, retrolental fibroplasia, hemangiomas, angiofibromas, psoriasis and rheumatoid arthritis. Also, angiogenesis inhibitors are useful to control solid tumor growth, such as, e.g. breast, prostate, melanoma, renal, colon, cervival cancer and the like; and metastasis.

The present invention thus also relates to compounds of formula (I) as defined hereinabove for use as a medicine.

In view of the usefulness of the subject compounds in the treatment or prevention of angiogenesis dependent disorders, the present invention provides a method of treating warm-blooded animals suffering from such disorders, said method comprising the systemic administration of a therapeutic effective amount of a compound of formula (I), a N-oxide or a pharmaceutically acceptable acid addition salt thereof.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from $1 \times 10^{-5}$ mg/kg to 10 mg/kg body weight, and in particular from 0.001 mg/kg to 1 mg/kg body weight. It may be appropriate to administer the required dose as two, three, four or more sub-doses at appropriate intervals throughout the day. Said sub-doses may be formulated as unit dosage forms, for example, containing 0.001 to 500 mg, and in particular 0.01 mg to 200 mg of active ingredient per unit dosage form.

The following examples are provided for purposes of illustration, not limition.

EXPERIMENTAL PART

Hereinafter "DMF" means N,N-dimethylformamide, "DCM" means dichloromethane, "DIPE" means diisopropylether and "THF" means tetrahydrofuran.

A. Preparation of the Intermediates

Example A.1

A mixture of 3-chloro-6-methylpyridazine (12.9 g) and thionyl chloride (119 g) was stirred for 1 night at reflux temperature. The mixture was evaporated, 200 ml of DCM was added and the mixture was cooled till –5° C. 1-Iminoethanamine hydrochloride (9.5 g) was added portionwise and the whole was stirred for 15 minutes. Then, sodium hydroxide (50%) (25 ml) was added dropwise (temp. <5° C.). The mixture was stirred till room temperature was reached. After stirring for 30 minutes, the layers were separated. The organic layer was dried, filtered and evaporated. The residue was purified by column chromatography, yielding 8.2 g (38.6%) of 3-chloro-6-(3-methyl-1,2,4-thiadiazol-5-yl)pyridazine; mp. 180.3° C. (intermediate 1-a).

Example A.2 a) A mixture of 3-chloro-6-methylpyridazine (19.3 g) in thionyl chloride (160 ml) was stirred and refluxed overnight. The mixture was evaporated, toluene (100 ml) was added and evaporated again, yielding 40 g (100%) of $\alpha,\alpha,3$-trichloro-6-pyridazine-methanesulfenyl chloride (intermediate 2-a).

b) A mixture of intermediate (2-a) (79.2 g) in DCM (600 ml) was stirred at 0° C. 2-(Phenylmethoxy)-ethanimidamide (40.1 g) was added. NaOH (50%, 60ml) was added dropwise at 0° C. The mixture was cooled and stirred at 0° C. for 1 hour. Water (300 ml) and DCM (400 ml) were added and the mixture was separated into its layers. The organic layer was dried, filtered and the solvent was evaporated. The residue was purified over silica gel on a glass filter and crystallized from 2-propanol. The precipitate was filtered off and dried, yielding 28 g (45%) of 3-chloro-6-[3-[(phenylmethoxy)methyl]-1,2,4-thiadiazol-5-yl] pyridazine (intermediate 2-b, mp; 109–110° C.).

Table 1 lists intermediates that were prepared analogously.

TABLE 1

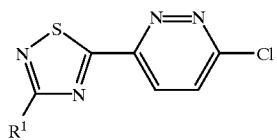

| Co. No. | Ex. No. | R¹ | R² | R³ | Physical Data |
|---|---|---|---|---|---|
| 1-a | A.1 | CH₃ | H | H | mp. 180.3° C. |
| 1-b | A.1 | S—CH₃ | H | H | mp. 169.9° C. |
| 1-c | A.1 | N(CH₃)₂ | H | H | mp. 193.7° C. |
| 1-d | A.1 | H | H | H | — |
| 1-e | A.1 | phenyl | H | H | mp. 191.6° C. |
| 1-f | A.1 | —C(CH₃)₃ | H | H | mp. 151.9° C. |
| 1-g | A.1 | —NH—C₆H₅ | H | H | mp. 243.8° C. |
| 1-h | A.1 | —NH₂ | H | H | — |
| 2-b | A.2 | C₆H₅—CH₂—O—CH₂ | H | H | mp. 109–110° C. |
| 2-c | A.2 | CH(CH₃)₂ | H | H | — |
| 2-d | A.2 | CH₂CH₃ | H | H | — |
| 2-e | A.2 | (CH₂)₃CH₃ | H | H | — |
| 2-f | A.2 | (CH₂)₂CH₃ | H | H | — |
| 2-g | A.2 | (CH₂)₄CH₃ | H | H | — |
| 2-h | A.2 | c.C₆H₁₁ | H | H | — |
| 2-i | A.2 | —NHCH₃ | H | H | — |
| 1-i | A.1 | CH₃ | —CH=CH—CH=CH—* | | mp. 152.5° C. |

*: R² and R³ taken together to form a bivalent radical

B. Preparation of the Final Compounds

Example B.1

A mixture of intermediate (1-a) (6.4 g), 1-[3-(trifluoromethyl)phenyl]piperazine (5.3 g) and sodium carbonate (8.5 g) in DMF (200ml) was stirred at 60° C. overnight. The mixture was poured into ice water and filtered off. The precipitate was dissolved in DCM and washed with water. The organic layer was dried, filtered off and evaporated. The residue was purified by column chromatography over silica gel (eluent: CHCl₃/CH₃OH 99.5/0.5). The pure fractions were collected and evaporated. The residue was crystallized from 2-propanol, yielding 2.3 g (24.6%) of 3-(3-methyl-1,2,4-thiadiazol-5-yl)-6-[4-[3-(trifluoromethyl)phenyl]-1-piperazinyl]pyridazine; mp. 173.2° C. (comp. 1).

Example B.2

At room temperature, 4-fluorophenol (1.2 g) was added to a solution of triphenylphosphine (2.9 g) in THF (200 ml) and the mixture was stirred at room temperature for 30 min. Diethyl azodicarboxylate (1.9 g) in a little THF was added dropwise at room temperature and the mixture was stirred for 5 min. 1-[6-(3-methyl-1,2,4-thiadiazol-5-yl)-3-pyridazinyl]-4-piperidine-methanol (3 g) in a little THF was added dropwise at room temperature and the mixture was stirred at room temperature for 2 hours. The solvent was evaporated and the residue was crystallized from 2-propanol. The precipitate was filtered off and dried, yielding: 1.66 g (43%) of 3-[4-[(4-fluorophenoxy)methyl]-1-piperidinyl]-6-(3-methyl-1,2,4-thiadiazol-5-yl)pyridazine (compound 55).

Example B.3

A mixture of 3,5-bis(trifluoromethyl)-benzoyl chloride (1.1 g) and triethylamine (0.4 g) in DCM (40 ml) was stirred. 3-(3-methyl-1,2,4-thiadiazol-5-yl)-6-( 1-piperazinyl)-pyridazine (1.1 g) was added portionwise. The mixture was stirred at room temperature for 3 hours. Triethylamine was added. The mixture was stirred at room temperature for 1 hour. Water was added and the mixture was extracted three times with DCM. The combined organic layer was dried, filtered and the solvent was evaporated. The residue was crystallized from methanol. The precipitate was filtered off and dried, yielding 0.91 g (45%) of 1-[3,5-bis(trifluoromethyl)benzoyl]-4-[6-(3-methyl-1,2,4-thiadiazol-5-yl)-3-pyridazinyl]piperazine (compound 131).

Example B.4

A mixture of compound 1 (3 g), N-bromosuccinimide (1.3 g) and 3-chloroperoxybenzoic acid (catalytic amount) in carbon tetrachloride (100 ml) was stirred overnight. The precipitate was filtered off, dried, and taken up in a mixture of N-bromosuccinimide (1.3 g) and 3-chloroperoxybenzoic acid (catalytic amount) in carbon tetrachloride (100 ml). The mixture was stirred and refluxed for 48 hours. The precipitate was filtered off, dried, and purified by column chromatography (eluent: NH₄OAc(0.5% in H₂O)/CH₃OH 30/70). The pure fractions were collected and the solvent was evaporated. The residue was crystallized from CH₃OH/CH₂Cl₂. The precipitate was filtered off and dried, yielding 0.77 g (21.5%) of 3-[4-[4-bromo-3-(trifluoromethyl)phenyl]-1-piperazinyl]-6-(3-methyl-1,2,4-thiadiazol-5-yl)pyridazine (compound 88).

In an analogous way, 1-[1-[4,4-bis(4-fluorophenyl)butyl]-4-piperidinyl]-4-(phenylmethyl)piperazine trihydrochloride (compound 90) was also prepared.

Example B.5

3-Chloroperoxybenzoic acid (0.9 g) was added in one portion to a solution of compound 53 (1.9 g) in DCM (50 ml), stirred at room temperature. The resulting reaction mixture was stirred for one hour at room temperature. The solvent was evaporated and the residue was dissolved in 2-propanol and converted into the hydrochloric acid salt (1:2) with HCl/2-propanol. The precipitate was filtered off and dried, yielding 1.9 g (90.3%) of 3-(3-methyl-1,2,4-thiadiazol-5-yl)-6-[4-[3-(trifluoromethyl)phenyl]-1- piperazinyl]-1-piperidinyl]pyridazine,piperazine-N1-oxide dihydrochloride (compound 162).

Example B.6 a) Hydrogen peroxide (1.22 g, 30%) was added at 0° C. to a mixture of dichloromaleic anhydride (2.17 g) in DCM (30 ml) under nitrogen flow. The mixture was stirred at 0° C. for 2 hours. 3-Chloro-6-methylpyridazine (1.4 g) was added at 0° C. The mixture was stirred and refluxed overnight, then washed twice with an aqueous NaHCO₃ solution, once with an aqueous Na₂SO₃ solution and once with H₂O. The combined organic layer was dried, filtered and the solvent was evaporated. The residue was used in the next step without further purification (intermediate 3).

b) A mixture of intermediate 3 (3.6 g), 1-(4-piperidinyl)-4-[3-(trifluoromethyl)phenyl]-piperazine (5 g) and Na₂CO₃ (3.4 g) in DMF (80 ml) was stirred at 60° C. overnight. The mixture was cooled, poured out into ice water (400 ml) and stirred for 1 hour. The precipitate was filtered off, dried and purified over silica gel on a glass filter (eluent: CH₂Cl₂/CH₃OH 100/0, 97.5/2.5 and 95/5). Two pure fractions were collected and their solvents were evaporated. The first fraction was crystallized from CH₃OH, yielding 1.7 g (21 %) of 3-(3-methyl-1,2,4-thiadiazol-5-yl)-6-[4-[4-[3-(trifluoromethyl)phenyl]-1-piperazinyl]-1-piperidinyl] pyridazine,2-oxide (compound 165). The other fraction was scratched, filtered off and dried, yielding 0.75 g (9%) of 3-(3-methyl-1,2,4-thiadiazol-5-yl)-6-[4-[4-[3-(trifluoromethyl)phenyl]-1-piperazinyl]-1-piperidinyl] pyridazine, 1-oxide (compound 166).

Tables 2 to 11 list the compounds that were prepared according to one of the above examples and table 12 lists both the experimental (column heading "exp.") and theoretical (column heading "theor.") elemental analysis values for carbon, hydrogen and nitrogen of the compounds as prepared in the experimental part hereinabove.

TABLE 2

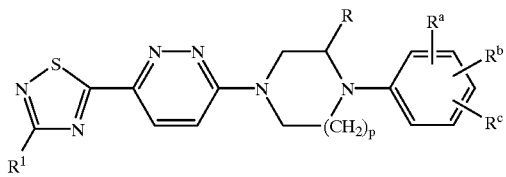

| Co. No. | Ex. No. | R¹ | R | p | Rᵃ | Rᵇ | Rᶜ | Physical data |
|---|---|---|---|---|---|---|---|---|
| 1 | B.1 | CH₃ | H | 1 | 3-CF₃ | H | H | mp. 173.2° C. |
| 2 | B.1 | CH₃ | H | 1 | 3-Cl | H | H | mp. 174.3° C. |
| 3 | B.1 | CH₃ | H | 1 | 2-OCH₃ | H | H | mp. 220.5° C. |
| 4 | B.1 | CH₃ | H | 1 | H | H | H | mp. 213.1° C. |
| 5 | B.1 | CH₃ | H | 1 | 3-CH₃ | H | H | mp. 170.2° C. |
| 6 | B.1 | N(CH₃)₂ | H | 1 | 3-CF₃ | H | H | mp. 206.3° C. |
| 7 | B.1 | S—CH₃ | H | 1 | 3-CF₃ | H | H | mp. 215.9° C. |
| 8 | B.1 | H | H | 1 | 3-Cl | H | H | mp. 177.3° C. |
| 9 | B.1 | S-CH₃ | H | 1 | 3-Cl | H | H | mp. 206.0° C. |
| 10 | B.1 | CH₃ | H | 2 | 3-Cl | H | H | mp. 156.7° C. |
| 11 | B.1 | CH₃ | H | 1 | 3-CF₃ | 4-Cl | H | mp. 200.2° C. |
| 12 | B.1 | CH₃ | H | 1 | 3-F | H | H | mp. 180.1° C. |
| 13 | B.1 | CH₃ | CH₃ | 1 | 3-Cl | H | H | mp. 155.5° C. |
| 14 | B.1 | CH₃ | H | 1 | 2-Cl | H | H | mp. 198.5° C. |
| 15 | B.1 | CH₃ | H | 1 | 4-Cl | H | H | mp. 236.2° C. |
| 16 | B.1 | C(CH₃)₃ | H | 1 | 3-Cl | H | H | mp. 161.8° C. |
| 17 | B.1 | phenyl | H | 1 | 3-CF₃ | H | H | mp. 223.0° C. |
| 18 | B.1 | CH₃ | H | 1 | 4-F | H | H | mp. 197.4° C. |
| 19 | B.1 | CH₃ | H | 1 | 3-OCH₃ | H | H | mp. 179.9° C. |
| 20 | B.1 | CH₃ | H | 1 | 4-CF₃ | H | H | mp. 229.4° C. |
| 21 | B.1 | CH₃ | H | 1 | 3-Cl | 4-Cl | H | mp. 202.1° C. |
| 22 | B.1 | CH(CH₃)₂ | H | 1 | 3-CF₃ | H | H | mp. 162.8° C. |
| 23 | B.1 | CH₃ | H | 1 | 3-Cl | 5-Cl | H | mp. 191.2° C. |
| 24 | B.1 | CH₃ | H | 1 | 2-Cl | 3-Cl | H | mp. 192.0° C. |
| 25 | B.1 | CH₂CH₃ | H | 1 | 3-CF₃ | H | H | mp. 174.6° C. |
| 26 | B.1 | (CH₂)₃CH₃ | H | 1 | 3-CF₃ | H | H | mp. 144.4° C. |
| 27 | B.1 | CH₃ | H | 1 | 2-Cl | 5-Cl | H | mp. 191.5° C. |
| 28 | B.1 | (CH₂)₂CH₃ | H | 1 | 3-CF₃ | H | H | mp. 146.2° C. |
| 29 | B.1 | (CH₂)₄CH₃ | H | 1 | 3-CF₃ | H | H | mp. 131.4° C.; .HCl |
| 67 | B.1 | c.C₆H₁₁(*) | H | 1 | 3-CF₃ | H | H | — |
| 68 | B.1 | CH₃ | H | 1 | 3-COOC₂H₅ | H | H | — |
| 69 | B.1 | CH₃ | H | 1 | 2-CH₃ | 3-CH₃ | H | mp. 191.6° C. |
| 71 | B.1 | CH₃ | H | 1 | 3-OH | H | H | — |
| 72 | B.1 | CH₃ | H | 1 | 3-Br | H | H | — |
| 73 | B.1 | CH₃ | H | 1 | 2-Br | 4-NH₂ | H | — |
| 74 | B.1 | CH₃ | H | 1 | 3-CF₃ | 5-CF₃ | H | — |
| 75 | B.1 | CH₃ | H | 1 | 2-Cl | 5-OCH₃ | H | — |
| 76 | B.1 | CH₃ | H | 1 | 2-CF₃ | H | H | — |
| 77 | B.1 | CH₃ | H | 1 | 2-Cl | 4-Cl | H | — |
| 78 | B.1 | CH₃ | H | 1 | 3-NH₂ | H | H | — |
| 79 | B.1 | CH₃ | H | 1 | 3-NH₂ | 4-NO₂ | H | — |

TABLE 2-continued

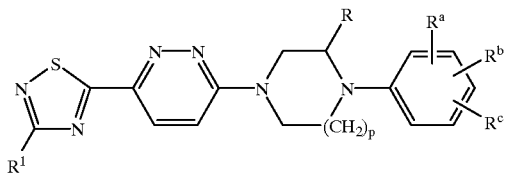

| Co. No. | Ex. No. | R¹ | R | p | Rᵃ | Rᵇ | Rᶜ | Physical data |
|---|---|---|---|---|---|---|---|---|
| 80 | B.1 | $CH_3$ | H | 1 | 2-Br | 3-$NH_2$ | 4-$NO_2$ | — |
| 81 | B.1 | $CH_3$ | H | 1 | 2-$NO_2$ | 4-Br | 6-$NO_2$ | — |
| 82 | B.1 | $CH_3$ | H | 1 | 2-Cl | 4-Cl | 5-Cl | — |
| 83 | B.1 | $CH_3$ | H | 1 | 3-$COOC_2H_5$ | 5-$CF_3$ | H | — |
| 84 | B.1 | $CH_3$ | H | 1 | 3-$NO_2$ | H | H | — |
| 85 | B.1 | $CH_3$ | H | 1 | 2-$NO_2$ | 4-Br | H | — |
| 86 | B.1 | $CH_3$ | H | 1 | 2-$NH_2$ | 4-Br | H | — |
| 87 | B.1 | $CH_3$ | H | 1 | 3-$NO_2$ | 5-$CF_3$ | H | — |
| 88 | B.4 | $CH_3$ | H | 1 | 3-$CF_3$ | 4-Br | H | — |
| 89 | B.1 | $CH_3$ | H | 1 | 3-$CF_3$ | 5-$NH_2$ | H | — |
| 90 | B.4 | $CH_3$ | H | 1 | 2-Br | 4-Br | 5-$NH_2$ | — |
| 91 | B.1 | $CH_3$ | H | 1 | 2-Cl | 6-Cl | H | — |
| 92 | B.1 | H | H | 1 | 3-$CF_3$ | H | H | — |
| 93 | B.1 | H | H | 1 | 3-$CF_3$ | 4-Cl | H | — |
| 94 | B.1 | H | H | 1 | 3-Cl | 5-Cl | H | — |
| 95 | B.1 | H | H | 1 | 3-Br | H | H | — |
| 96 | B.1 | H | $CH_3$ | 1 | 3-Cl | H | H | — |
| 97 | B.1 | H | H | 1 | 3-$CF_3$ | 5-$CF_3$ | H | — |
| 98 | B.1 | $NH_2$ | H | 1 | 3-$CF_3$ | H | H | — |
| 99 | B.1 | —$NHCH_3$ | H | 1 | 3-$CF_3$ | H | H | — |
| 100 | B.1 | —$N(CH_3)_2$ | H | 1 | 3-$CF_3$ | 4-Cl | H | — |
| 101 | B.1 | —$N(CH_3)_2$ | H | 1 | 2-Cl | 5-$OCH_3$ | H | — |
| 102 | B.1 | —$N(CH_3)_2$ | $CH_3$ | 1 | 3-Cl | H | H | — |
| 103 | B.1 | —$N(CH_3)_2$ | H | 1 | 3-Br | H | H | — |
| 104 | B.1 | —$N(CH_3)_2$ | H | 1 | 2-Cl | 4-Cl | 5-Cl | mp. 208° C. |
| 105 | B.1 | —$N(CH_3)_2$ | H | 1 | 3-$CF_3$ | 5-$CF_3$ | H | — |
| 106 | B.1 | —$N(CH_3)_2$ | H | 1 | 3-Cl | 5-Cl | H | — |
| 70 | B.1 | —$NHC_6H_5$ | H | 1 | 3-$CF_3$ | H | H | — |

(*): c.$C_6H_{11}$ means cyclohexyl

TABLE 3

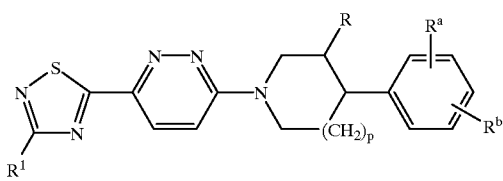

| Co. No. | Ex. No. | R¹ | R | p | Rᵃ | Rᵇ | Physical data |
|---|---|---|---|---|---|---|---|
| 30 | B.1 | $CH_3$ | H | 0 | 3-$CF_3$ | H | mp. 190.2° C. |
| 31 | B.1 | $CH_3$ | H | 1 | 3-$CF_3$ | H | mp. 138.3° C. |
| 32 | B.1 | $CH_3$ | H | 2 | 3-$CF_3$ | H | mp. 135.0° C. |
| 107 | B.1 | $CH_3$ | H | 1 | 4-$COOC_2H_5$ | H | .HCl |
| 108 | B.1 | $CH_3$ | $CH_3$ | 1 | 3-$CF_3$ | H | (cis) |
| 109 | B.1 | $CH_3$ | H | 1 | 3-$CH_3$ | 4-$CH_3$ | — |
| 110 | B.1 | $CH_3$ | —$N(CH_3)_2$ | 1 | H | H | — |
| 111 | B.1 | $CH_3$ | H | 1 | 3-$CF_3$ | 5-$CF_3$ | — |
| 112 | B.1 | $CH_3$ | —$NHCOCH_3$ | 1 | 3-$CF_3$ | H | (cis) |
| 113 | B.1 | H | $CH_3$ | 1 | 3-$CF_3$ | H | — |
| 114 | B.1 | —$N(CH_3)_2$ | H | 1 | 3-$CF_3$ | H | .HCl |
| 115 | B.1 | —$N(CH_3)_2$ | $CH_3$ | 1 | 3-$CF_3$ | H | (cis); mp. 159° C. |

TABLE 4

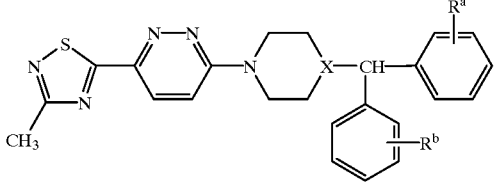

| Co. No. | Ex. No. | X | R^a | R^b | Physical data |
|---|---|---|---|---|---|
| 33 | B.1 | N | H | H | mp. 193.4° C. |
| 34 | B.1 | N | 4-F | 4-F | mp. 187.3° C. |
| 35 | B.1 | CH | H | H | mp. 188.4° C. |

TABLE 5

| Co. No. | Ex. No. | $R^1$ | X | $R^a$ | Physical data |
|---|---|---|---|---|---|
| 36 | B.1 | $CH_3$ | CH | 4-F | mp. 164.2° C. |
| 37 | B.1 | $CH_3$ | N | 3-Cl | mp. 169.9° C. |
| 38 | B.1 | $CH_3$ | N | 4-F | mp. 195.0° C. |
| 39 | B.1 | $CH_3$ | N | 3-$CF_3$ | mp. 167.4° C. |
| 116 | B.1 | $CH_3$ | CH | 3-Cl | — |
| 132 | B.1 | $CH_3$ | CH | 3-$CF_3$ | — |
| 117 | B.1 | H | CH | 3-$CF_3$ | — |

TABLE 6

| Co. No. | Ex. No. | $R^1$ | X | L | Physical data |
|---|---|---|---|---|---|
| 40 | B.1 | $CH_3$ | N | 1-methyl-2,2-dimethyl-tetrahydronaphthalenyl | mp. 182.6° C. |
| 41 | B.1 | $CH_3$ | N | 4-methyl-thiochroman-4-yl | mp. 195.8° C. |
| 42 | B.1 | $CH_3$ | N | 1-methyl-naphthalenyl | mp. 204.2° C. |
| 43 | B.1 | $CH_3$ | N | 1-methyl-2,2-dimethyl-indanyl | mp. 179.8° C. |

TABLE 6-continued
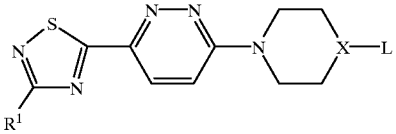
| Co. No. | Ex. No. | R₁ | X | L | Physical data |
|---|---|---|---|---|---|
| 44 | B.1 | CH₃ | N | 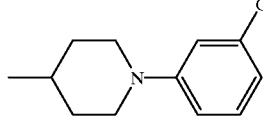 | mp. 185.3° C. |
| 45 | B.1 | CH₃ | CH | 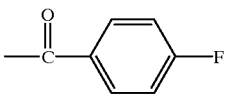 | mp. 203.0° C. |
| 46 | B.1 | CH₃ | CH | 4-fluorophenoxy | mp. 164.9° C. |
| 47 | B.1 | CH₃ | CH | 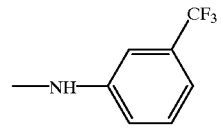 | mp. 145.1° C. |
| 48 | B.1 | CH₃ | CH | 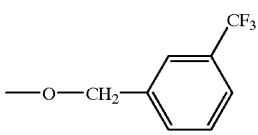 | mp. 95.5° C. |
| 49 | B.1 | CH₃ | CH | 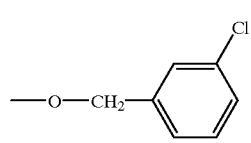 | mp. 87.7° C. |
| 50 | B.1 | CH₃ | CH | 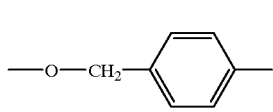 | mp. 133.2° C. |
| 51 | B.1 | CH₃ | CH | 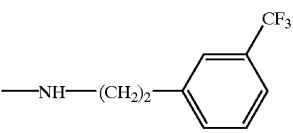 | — |
| 52 | B.1 | CH₃ | CH | 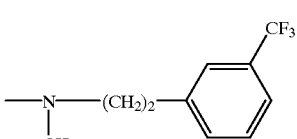 | mp. 136.4° C. |
| 54 | B.1 | CH₃ | CH | —O—CH(C₆H₅)₂ | mp. 149.9° C. |
| 118 | B.1 | CH₃ | CH | —NH—CO—C₆H₅ | mp. 269.1° C. |

TABLE 6-continued

[Structure: 1,2,4-thiadiazole with R¹ at 3-position, linked to pyridazine, linked to piperazine ring with X—L]

| Co. No. | Ex. No. | R¹ | X | L | Physical data |
|---|---|---|---|---|---|
| 119 | B.1 | CH₃ | CH | 1-methyl-2-oxo-benzimidazol-3-yl | mp. >300° C. |
| 120 | B.1 | CH₃ | CH | 3-methyl-1H-indol-1-yl | mp. 199.5° C. |
| 121 | B.1 | CH₃ | CH | N-methyl-N-(benzothiazol-2-yl)amino | mp. 210.2° C. |
| 122 | B.1 | CH₃ | N | 6-chloro-3-methyl-pyridazinyl | mp. 291.6° C. |
| 123 | B.1 | CH₃ | N | 2-pyrimidinyl | mp. 232.1° C. |
| 124 | B.1 | CH₃ | CH | 3-chlorophenoxy | mp. 94.3° C. |
| 125 | B.1 | CH₃ | N | (E); —CH₂—CH=CH—C₆H₅ | mp. 166.9° C. |
| 126 | B.1 | CH₃ | CH | 1-methyl-4-(3-trifluoromethylphenyl)piperidinyl | mp. 163.4° C. |
| 127 | B.1 | CH₃ | CH | —N(CH₃)—(CH₂)₂—NH—(3-trifluoromethylphenyl) | mp. 112.3° C. |
| 128 | B.1 | CH₃ | CH | (4-fluorophenyl)amino | mp. 187.5° C. |
| 129 | B.1 | CH₃ | CH | 3-trifluoromethylphenyoxy | — |
| 130 | B.1 | CH₃ | CH | 3-trifluoromethylbenzoyl | — |

TABLE 6-continued

| Co. No. | Ex. No. | R¹ | X | L | Physical data |
|---|---|---|---|---|---|
| 131 | B.1 | $CH_3$ | N | 3,5-bis(trifluoromethyl)benzoyl | — |
| 133 | B.1 | $CH_3$ | N | 6-fluoro-3-methyl-1,2-benzisoxazol-yl | — |
| 134 | B.1 | $CH_3$ | CH | 1-(3-trifluoromethylphenyl)-1-hydroxyethyl | — |
| 135 | B.1 | $CH_3$ | CH | 3-chlorobenzoyl | — |
| 136 | B.1 | $CH_3$ | CH | 1-cyano-1-(3-trifluoromethylphenyl)methyl | — |
| 137 | B.1 | $CH_3$ | CH | N-methyl-N-[(3-trifluoromethylphenyl)methyl]amino | — |
| 138 | B.1 | $CH_3$ | CH | 1-cyano-1-(3-chlorophenyl)methyl | — |
| 139 | B.1 | $CH_3$ | CH | (3-chlorophenyl)thio | — |

TABLE 6-continued
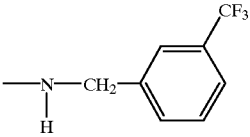
| Co. No. | Ex. No. | R₁ | X | L | Physical data |
|---|---|---|---|---|---|
| 140 | B.1 | CH₃ | CH | 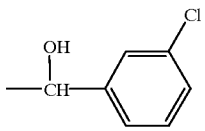 | — |
| 141 | B.1 | CH₃ | CH | 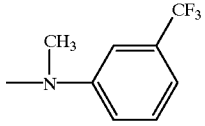 | — |
| 142 | B.1 | CH₃ | CH | 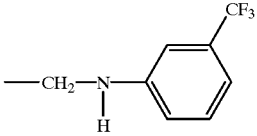 | — |
| 143 | B.1 | CH₃ | CH | 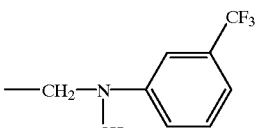 | — |
| 144 | B.1 | CH₃ | CH | 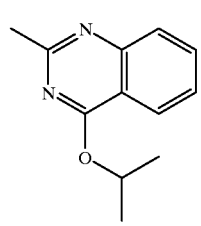 | — |
| 145 | B.1 | CH₃ | CH | 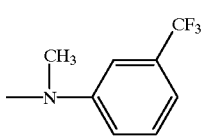 | — |
| 146 | B.1 | H | CH |  | — |

TABLE 6-continued

[Structure: 1,2,4-thiadiazole with R¹ substituent, linked to pyridazine, linked to piperazine ring with X—L substituent]

| Co. No. | Ex. No. | R¹ | X | L | Physical data |
|---|---|---|---|---|---|
| 147 | B.1 | H | CH | 3-(trifluoromethyl)benzoyl [—C(=O)—C₆H₄—CF₃] | — |
| 148 | B.1 | H | CH | 3-trifluoromethylbenzyloxy | — |
| 149 | B.1 | H | CH | 3-trifluoromethylphenyloxy | — |
| 150 | B.1 | H | CH | 3-(trifluoromethyl)phenylamino [—NH—C₆H₄—CF₃] | — |
| 151 | B.1 | —N(CH₃)₂ | CH | N-methyl-3-(trifluoromethyl)phenylamino [—N(CH₃)—C₆H₄—CF₃] | — |
| 152 | B.1 | —N(CH₃)₂ | CH | 3-trifluoromethylbenzyloxy | — |
| 153 | B.1 | —N(CH₃)₂ | CH | 3-trifluoromethylbenzyloxy | — |
| 154 | B.1 | —N(CH₃)₂ | CH | 3-chlorophenylthio [—S—C₆H₄—Cl] | — |
| 155 | B.1 | —N(CH₃)₂ | CH | 3-(trifluoromethyl)phenylamino [—NH—C₆H₄—CF₃] | — |

TABLE 7

[Structure: 1,2,4-thiadiazole with R¹ substituent, linked to pyridazine, linked to piperazine with X-Alk-O—Ar substituent]

| Co. No. | Ex. No. | R¹ | X | Alk | Ar | Physical data |
|---|---|---|---|---|---|---|
| 55 | B.2 | CH₃ | CH | CH₂ | 4-fluorophenyl | mp. 161.3° C. |
| 56 | B.2 | CH₃ | CH | CH₂ | 3-chlorophenyl | mp. 137.0° C. |

TABLE 7-continued

[Structure: thiadiazole-R¹ connected to pyridazine connected to piperidine-X-Alk-O-Ar]

| Co. No. | Ex. No. | R¹ | X | Alk | Ar | Physical data |
|---|---|---|---|---|---|---|
| 57 | B.2 | CH₃ | CH | (CH₂)₂ | 4-(3-ethyl-1,2,4-oxadiazol-5-yl)phenyl | mp. 175.5° C. |
| 60 | B.2 | CH₃ | CH | (CH₂)₂ | 4-(5-ethyl-1,2,4-oxadiazol-3-yl)phenyl | mp. 170.5° C. |
| 61 | B.2 | CH₃ | CH | (CH₂)₂ | 4-(ethoxycarbonyl)phenyl | mp. 148.2° C. |
| 62 | B.2 | CH₃ | CH | (CH₂)₂ | 4-fluorophenyl | mp. 146.2° C. |
| 63 | B.2 | CH₃ | CH | (CH₂)₂ | 3-chlorophenyl | mp. 137.8° C. |
| 64 | B.2 | CH₃ | N | (CH₂)₂ | 4-(5-ethyl-1,2,4-oxadiazol-3-yl)phenyl | mp. 164.4° C. |
| 65 | B.2 | CH₃ | N | (CH₂)₂ | 4-(3-ethyl-1,2,4-oxadiazol-5-yl)phenyl | mp. 162.4° C. |
| 156 | B.1 | CH₃ | N | (CH₂)₂ | 4-(ethoxycarbonyl)phenyl | mp. 168.0° C. |
| 157 | B.1 | H | CH | CH₂ | 3-trifluoromethylphenyl | — |
| 158 | B.1 | —N(CH₃)₂ | CH | CH₂ | 3-trifluoromethylphenyl | — |

TABLE 8

[Structure: thiadiazole-R¹ connected to pyridazine connected to tetrahydropyridine with Ar and R substituents]

| Co. No. | Ex. No. | R¹ | R | Ar | Physical data |
|---|---|---|---|---|---|
| 66 | B.2 | CH₃ | H | 3-trifluoromethylphenyl | mp. 171.1° C. |
| 159 | B.1 | —N(CH₃)₂ | CH₃ | 3-trifluoromethylphenyl | — |

TABLE 9

[Structure: thiadiazole-R¹ connected to pyridazine with (O)ₓ and (O)ᵧ on the two N's, linked to piperidine, then to piperazine with (O)ᵤ on one N, terminated with Ar]

| Co. No. | Ex. No. | x | y | z | R¹ | Ar | Physical data |
|---|---|---|---|---|---|---|---|
| 53 | B.1 | 0 | 0 | 0 | CH₃ | 3-trifluoromethylphenyl | mp. 184.2° C. |
| 160 | B.1 | 0 | 0 | 0 | CH₃ | 3,5-dichlorophenyl | — |
| 161 | B.1 | 0 | 0 | 0 | CH₃ | 3,5-bis(trifluoromethyl)phenyl | — |
| 162 | B.5 | 0 | 0 | 1 | CH₃ | 3-trifluoromethylphenyl | — |
| 163 | B.1 | 0 | 0 | 0 | H | 3-trifluoromethylphenyl | — |
| 164 | B.1 | 0 | 0 | 0 | —N(CH₃)₂ | 3-trifluoromethylphenyl | — |
| 165 | B.6 | 1 | 0 | 0 | CH₃ | 3-trifluoromethylphenyl | — |
| 166 | B.6 | 0 | 1 | 0 | CH₃ | 3-trifluoromethylphenyl | — |
| 167 | B.1 | 0 | 0 | 0 | —CH₂OCH₂C₆H₅ | 3-trifluoromethylphenyl | — |
| 168 | (*) | 0 | 0 | 0 | —CH₂OH | 3-trifluoromethylphenyl | — |

(*): prepared by hydrolysing compound 167 under acidic conditions

TABLE 10

[Structure: thiadiazole-R¹ connected to pyridazine, linked to N with (CH₂)ₘ and (CH₂)ₙ forming ring with X-R, terminated with L]

| Co. No. | Ex. No. | R¹ | m | n | X | R | L | Physical data |
|---|---|---|---|---|---|---|---|---|
| 169 | B.1 | CH₃ | 2 | 1 | CH | H | —NH-(3-CF₃-phenyl) | mp. 173.1° C. |
| 170 | B.1 | CH₃ | 3 | 1 | CH | H | 3-trifluoromethylphenyl | — |
| 171 | B.1 | CH₃ | 3 | 1 | CH | H | 3-trifluoromethylbenzyl | .HCl |
| 172 | B.1 | CH₃ | 3 | 1 | CH | H | —NH-(3-CF₃-phenyl) | .2 HCl.H₂O |
| 173 | B.1 | CH₃ | 3 | 1 | CH | H | —CH₂—NH-(3-CF₃-phenyl) | mp. 145.5° C. |
| 174 | B.1 | CH₃ | 3 | 1 | CH | 4-OH | N-methylpiperazinyl-(3-CF₃-phenyl) | — |

TABLE 10-continued
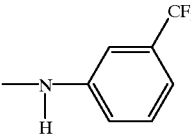
| Co. No. | Ex. No. | R¹ | m | n | X | R | L | Physical data |
|---|---|---|---|---|---|---|---|---|
| 175 | B.1 | CH₃ | 2 | 2 | CH | 3-OCH₃ | 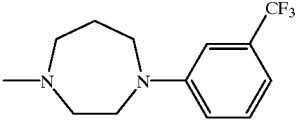 | (cis) |
| 176 | B.1 | CH₃ | 2 | 1 | CH | H | 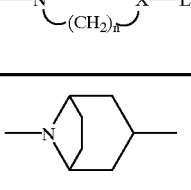 | — |
TABLE 11
| No. Co. | Ex. No. | R² | R³ | —N⟨(CH₂)ₘ/(CH₂)ₙ⟩X—L | L | Physical data |
|---|---|---|---|---|---|---|
| 177 | B.1 | H | H | 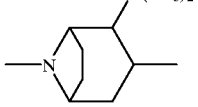 | 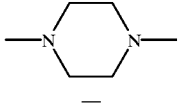 | mp. 141.0° C. |
| 178 | B.1 | H | H | | —CH₂— | mp. 223.2° C.; .(E)—C⁴H₄O₄ |
| 58 | B.1 | H | H | | —O— | (2-exo, 3-endo; .2 HCl) |
| 59 | B.1 | —CH=CH—CH=CH—* | | | | mp. 211.4° C. |
*: R² and R³ taken together to form a bivalent radical

TABLE 12

| Comp. No. | Carbon Exp. | Carbon Theor. | Hydrogen Exp. | Hydrogen Theor. | Nitrogen Exp. | Nitrogen Theor. |
|---|---|---|---|---|---|---|
| 74 | 48.02 | 48.10 | 3.03 | 3.40 | 17.69 | 17.71 |
| 75 | 53.21 | 53.66 | 4.39 | 4.75 | 20.79 | 20.86 |
| 76 | 53.16 | 53.19 | 3.89 | 4.22 | 20.84 | 20.68 |
| 77 | 49.42 | 50.13 | 3.56 | 3.96 | 20.29 | 20.63 |
| 78 | 56.69 | 57.77 | 5.09 | 5.42 | 27.35 | 27.74 |
| 79 | 50.59 | 51.25 | 4.22 | 4.55 | 27.86 | 28.12 |
| 80 | 42.24 | 42.78 | 3.31 | 3.59 | 23.05 | 23.47 |
| 81 | 39.62 | 40.25 | 2.78 | 2.98 | 21.84 | 22.09 |
| 82 | 46.23 | 46.22 | 3.33 | 3.42 | 19.08 | 19.02 |
| 83 | 52.99 | 52.71 | 4.18 | 4.42 | 17.50 | 17.56 |
| 84 | 52.46 | 53.25 | 4.15 | 4.47 | 25.75 | 25.57 |
| 86 | 46.86 | 47.23 | 4.09 | 4.20 | 22.54 | 22.68 |
| 87 | 47.59 | 47.89 | 3.48 | 3.57 | 21.90 | 21.72 |
| 88 | 44.45 | 44.55 | 3.29 | 3.32 | 17.58 | 17.32 |
| 89 | 51.29 | 51.30 | 4.31 | 4.30 | 23.43 | 23.26 |
| 90 | 39.96 | 39.94 | 3.15 | 3.35 | 19.49 | 19.18 |
| 91 | 50.04 | 50.13 | 3.88 | 3.96 | 20.59 | 20.63 |
| 93 | 47.33 | 47.84 | 3.22 | 3.31 | 19.77 | 19.69 |
| 95 | 47.38 | 47.65 | 3.69 | 3.75 | 21.19 | 20.84 |
| 96 | 54.31 | 54.76 | 4.62 | 4.60 | 23.12 | 22.54 |
| 97 | 47.15 | 46.96 | 3.03 | 3.06 | 18.64 | 18.25 |
| 98 | 50.12 | 50.12 | 3.73 | 3.96 | 23.57 | 24.07 |
| 99 | 50.73 | 51.30 | 4.39 | 4.30 | 23.49 | 23.26 |
| 101 | 52.60 | 52.83 | 5.18 | 5.13 | 22.93 | 22.70 |
| 102 | 54.26 | 54.86 | 5.21 | 5.33 | 23.45 | 23.57 |
| 103 | 48.09 | 48.43 | 4.40 | 4.52 | 22.13 | 21.97 |
| 104 | 45.82 | 45.92 | 3.70 | 3.85 | 21.02 | 20.83 |
| 108 | 55.19 | 57.27 | 4.48 | 4.81 | 16.02 | 16.70 |
| 109 | 65.44 | 65.72 | 6.28 | 6.34 | 19.48 | 19.16 |
| 111 | 50.72 | 50.74 | 3.29 | 3.62 | 14.85 | 14.79 |
| 116 | 58.89 | 59.13 | 5.11 | 5.22 | 17.95 | 18.15 |
| 117 | 56.27 | 56.29 | 4.44 | 4.47 | 17.50 | 17.27 |
| 131 | 47.68 | 47.81 | 2.95 | 3.21 | 16.80 | 16.73 |
| 134 | 54.92 | 55.16 | 4.25 | 4.63 | 16.37 | 16.08 |
| 135 | 56.80 | 57.07 | 4.31 | 4.54 | 17.87 | 17.51 |
| 136 | 56.57 | 56.75 | 4.20 | 4.31 | 18.79 | 18.91 |
| 137 | 56.14 | 56.24 | 5.03 | 5.17 | 18.98 | 18.74 |
| 138 | 58.14 | 58.46 | 4.51 | 4.66 | 20.45 | 20.45 |
| 139 | 53.39 | 53.52 | 4.21 | 4.49 | 17.39 | 17.34 |
| 140 | 55.28 | 55.29 | 4.66 | 4.87 | 19.29 | 19.34 |
| 141 | 57.50 | 56.78 | 5.51 | 5.02 | 15.60 | 17.42 |
| 142 | 55.03 | 55.29 | 4.77 | 4.87 | 19.33 | 19.34 |
| 143 | 54.93 | 55.29 | 4.91 | 4.87 | 19.84 | 19.34 |
| 144 | 56.24 | 56.24 | 5.21 | 5.17 | 19.25 | 18.74 |
| 145 | 60.39 | 60.48 | 5.90 | 5.92 | 23.84 | 23.51 |
| 146 | 53.58 | 54.28 | 4.54 | 4.55 | 20.23 | 19.99 |
| 147 | 54.04 | 54.41 | 3.71 | 3.84 | 16.75 | 16.70 |
| 148 | 54.23 | 54.15 | 4.29 | 4.30 | 16.94 | 16.62 |
| 149 | 52.45 | 53.07 | 3.90 | 3.96 | 17.62 | 17.19 |
| 150 | 52.89 | 53.19 | 4.17 | 4.22 | 21.05 | 20.68 |
| 151 | 54.09 | 54.42 | 5.20 | 5.22 | 21.54 | 21.15 |
| 152 | 54.27 | 54.30 | 4.94 | 4.99 | 18.33 | 18.09 |
| 153 | 52.87 | 53.32 | 4.66 | 4.70 | 18.62 | 18.66 |
| 154 | 51.58 | 52.70 | 4.96 | 4.89 | 18.77 | 19.41 |
| 155 | 53.26 | 53.44 | 4.90 | 4.93 | 22.12 | 21.81 |
| 157 | 54.21 | 54.15 | 4.28 | 4.30 | 16.83 | 16.62 |
| 158 | 54.24 | 54.30 | 4.87 | 4.99 | 17.85 | 18.09 |
| 159 | 55.80 | 56.49 | 4.77 | 4.74 | 18.54 | 18.82 |
| 160 | 53.84 | 53.88 | 5.00 | 5.14 | 20.00 | 19.99 |
| 162 | 46.19 | 47.75 | 4.71 | 4.88 | 16.43 | 16.95 |
| 163 | 55.43 | 55.57 | 5.07 | 5.09 | 20.59 | 20.62 |
| 165 | 54.71 | 54.64 | 5.11 | 5.18 | 19.62 | 19.39 |
| 166 | 54.46 | 54.64 | 5.18 | 5.18 | 19.53 | 19.39 |
| 167 | 60.33 | 60.49 | 5.53 | 5.41 | 16.50 | 16.46 |
| 174 | 54.59 | 54.64 | 5.03 | 5.18 | 19.27 | 19.39 |

C. Pharmacological Examples

Example C.1

Angiogenosis inhibitory activity was measured in vitro using the rat aortic ring model of angiogenesis as described by Nicosia, R. F. and Ottinetti in "Laboratory Investigation", vol. 63, p. 115, 1990. The ability of compounds to inhibit microvessel formation was compared to velicle-treated control rings. Quantitation (microvessel area (following eight days in culture was performed using an image analysis system, consisting of a light microscope, a CCD camera and an automated, custom-designed image analysis program as described by Nissanov, J., Tuman, R. W., Gruver, L. M., and Fortunato, J. M. in "Laboratory Investigation", vol 73 (#5), p. 734, 1995. Compounds were tested at several concentrations for determination of inhibitory potency (IC50's). Several compounds, as listed in table 13, have an $IC_{50}$ value lower than 1 nM.

TABLE 13

| Co. No. | $IC_{50}$ (nM) |
|---|---|
| 1 | 0.3 |
| 2 | 0.6 |
| 13 | 0.8 |
| 23 | 0.05 |
| 24 | 0.3 |
| 27 | 0.2 |
| 31 | 0.052 |
| 32 | 0.9 |
| 44 | 0.7 |
| 48 | 0.5 |
| 53 | 0.3 |
| 56 | 0.9 |
| 66 | 0.3 |
| 72 | 0.5 |
| 74 | 0.05 |
| 75 | 0.6 |
| 76 | 0.2 |
| 82 | 0.8 |
| 85 | <0.1 |
| 108 | 0.2 |
| 111 | 0.2 |
| 130 | 0.3 |
| 132 | 0.2 |
| 134 | 0.6 |
| 135 | 0.5 |
| 137 | 0.5 |
| 138 | 0.2 |
| 139 | 0.5 |
| 142 | 0.3 |
| 160 | 0.2 |
| 161 | <0.1 |
| 169 | 0.8 |
| 177 | 0.7 |

Example C.2

The in vivo angiogenesis inhibitory activity was measured using the Matrigel model, as described in U.S. Pat. No. 5,382,514. Briefly, a liquid, containing extracts of murine basement membrane and an angiogenic growth factor (e.g. VEGF, bFGF, aFGF), was injected in a warm-blooded animal where it fonns a gel matrix. After a period of time, the gel is recovered from the anmimal and angiogenesis is quantitated. The test compounds were administered orally at a dose of 0.1 mg/kg. Compounds 2, 30, 31, 47, 53, 54, 74, 75, 82, 88, 134, 138 and 177 were found to inhibit angiogenesis by more than 70%.

D. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a N-oxide form, a pharmaceutically acceptable acid addition salt or a stereochemically isomeric form thereof.

Example D.1: Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example D.2: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example D.3: Film-coated tablets
Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.
Coating To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of olyvinylpyrrolidone and 30 ml of concen-trated colour suspension and the whole is homogenated. The tablet cores are coated with the thus obtained mixture in a coating apparatus.

Example D.4: Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

Example D.5: Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37–38° C. to form 100 suppositories each containing 30 mg/ml of the A.I.

What is claimed:
1. A compound of formula

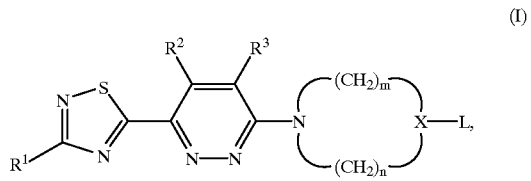

the N-oxide forms, the pharmaceutically acceptable acid addition salts and stereochemically isomeric forms thereof, wherein
X is CH or N; m is 2 or 3 and n is 1, 2 or 3; wherein 1 or 2 C-atoms of the $CH_2$ groups of the

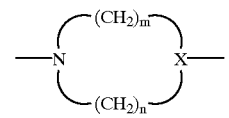

moiety, which may also contain one double bond, may be substituted with $C_{1-6}$alkyl, amino, aminocarbonyl, mono- or di($C_{1-6}$alkyl)amino, $C_{1-6}$alkyloxycarbonyl, $C_{1-6}$alkylcarbonylamino, hydroxy or $C_{1-6}$alkyloxy;
and/or 2 C-atoms of said $CH_2$ groups may be bridged with $C_{2-4}$alkanediyl;
$R^1$ is hydrogen, $C_{1-6}$alkyl, $C_{1-6}$alkyloxy, $C_{1-6}$alkylthio, amino, mono- or di($C_{1-6}$alkyl)amino, Ar, ArNH—, $C_{3-6}$cycloalkyl, hydroxymethyl or benzyloxymethyl;
$R^2$ and $R^3$ are hydrogen, or taken together may form a bivalent radical of formula

in case X represents CH then L is a radical $L^1$, $L^2$ or $L^3$; or
in case X represents N then L is a radical $L^2$ or $L^3$;
$L^1$ is Ar-$C_{1-6}$alkyloxy, Ar-oxy, Ar-thio, Ar-carbonylamino, di-Ar-methyloxy-, N-Ar-piperazinyl, N-Ar-homopiperazinyl, 2-benzimidazolinonyl, Ar—$NR^4$—, Ar-Alk-$NR^4$—, Ar—$NR^4$-Alk-$NR^5$— or Het-$NR^4$—;
$L^2$ is Ar, Ar-carbonyl, Ar—CH=CH—$CH_2$—, naphtalenyl or Het;
$L^3$ is $C_{1-6}$alkyl substituted with one or two radicals selected from Ar, Ar-oxy, or Ar-thio, further optionally substituted with cyano or hydroxy; 2,2-dimethyl-1,2,3,4-tetrahydro-naphtalenyl; 2,2-dimethyl-1H-2,3-dihydroindenyl; Ar-piperidinyl or Ar—$NR^4$-Alk-;
$R^4$ and $R^5$ are each independently selected from hydrogen or $C_{1-6}$alkyl;
Ar is phenyl; phenyl substituted with 1, 2 or 3 substituents each independently selected from halo, tmino, nitro, $C_{1-6}$alkyl, trihalomethyl, $C_{1-6}$alkyloxy, $C_{1-6}$alkyloxycarbonyl or hydroxy; phenyl substituted with an oxadiazole substituted with $C_{1-6}$alkyl;
Het is a monocyclic or bicyclic heterocycle; monocyclic heterocycles are pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; bicyclic heterocycles are indolyl, quinolinyl, quinazolinyl, quinoxalinyl, benzoxazolyl, benzisoxazolyl, benzothiazolyl, benzisothiazolyl, benzofuranyl, benzothienyl, benzopyranyl, benzothiopyranyl and thiochromanyl; each monocyclic and bicyclic heterocycle may optionally be substituted on a carbon atom by 1 or 2 substituents each independently selected from halo, $C_{1-4}$alkyl, $C_{1-4}$alkyloxy, or trihalomethyl; and Alk is $C_{1-6}$alkanediyl.

2. A compound according to claim 1 wherein X is CH or N, and the $CH_2$ groups of the

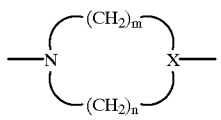

moiety are unsubstituted.

3. A compound according to claim 2 wherein $R^1$ is $C_{1-6}$alkyl, X is CH and m is 2 and n is 2.

4. A compound according to claim 2 wherein $R^1$ is $C_{1-6}$alkyl, X is N and m is 2 and n is 2.

5. A compound according to claim 2 wherein $R^1$ is methyl, $R^2$ and $R^3$ are hydrogen, X is CH or N and L is Ar-piperidinyl or phenyl substituted with 1, 2 or 3 substituents each independently selected from halo or trifluoromethyl.

6. A compound according to claim 2 wherein $R^1$ is hydrogen or di($C_{1-6}$alkyl)amino, $R^2$ and $R^3$ are hydrogen, and m is 2 and n is 2.

7. A compound according to claim 1 wherein the compound is selected from

3-[4-(3-chlorophenyl)-1-piperazinyl]-6-(3-methyl-1,2,4-thiadiazol-5-yl)pyridazine, 3-(3-methyl-1,2,4-thiadiazol-5-yl)-6-[4-[3-(trifluoromethyl)phenyl]-1-piperazinyl]pyridazine, 3-(3-methyl-1,2,4-thiadiazol-5-yl)-6-[4-[3-(trifluoromethyl)phenyl]-1-piperidinyl]pyridazine, 3-(3-methyl-1,2,4-thiadiazol-5-yl)-6-[4-[4-[3-(trifluoromethyl)phenyl]-1-piperazinyl]-1-piperidinyl]pyridazine, 3-(1,2,4-thiadiazol-5-yl)-6-[4-[3-(trifluoromethyl)phenyl]-1-piperazinyl]pyridazine, 1-[6-(3-methyl-1,2,4-thiadiazol-5-yl)-3-pyridazinyl]-N-[3-(trifluoromethyl)phenyl]-4-piperidinamine, and N,N-dimethyl-5-[6-[4-[3-(trifluoromethyl)phenyl]-1-piperazinyl]-3-pyridazinyl]-1,2,4-thiadiazol-3-amine; the stereochemically isomeric forms, pharmaceutically acceptable acid addition salts or the N-oxides thereof.

8. A composition comprising a pharmaceutically acceptable carrier, and as active ingredient a therapeutically effective amount of a compound as claimed in any one of claims 1 to 7.

9. A process of preparing a compound as claimed in claim 1, characterized by a) N-alkylating a pyridazine of formula (II), wherein $R^1$, $R^2$ and $R^3$ are defined as in claim 1 and W is an appropriate leaving group, with an amine of formula (III)

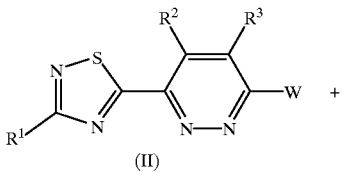

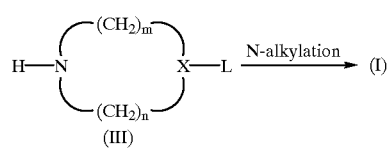

wherein X, L, m and n are defined is in claim 1, in a reaction-inert solvent, preferably in the presence of a suitable base;

b) N-alkylating a pyridazinamine of formula (IV), wherein $R^1$, $R^2$, $R^3$, m and n are defined as in claim 1, with an intermediate of formula (V),

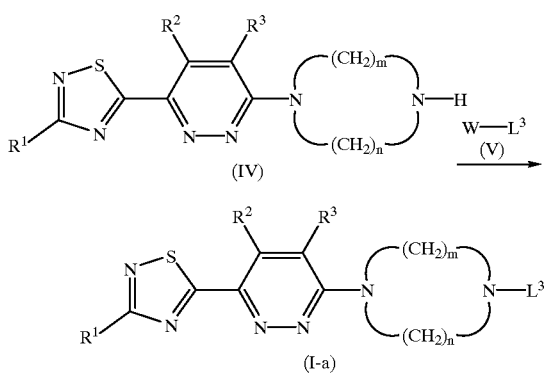

wherein W is an appropriate leaving group and $L^3$ is defined as in claim 1, in a reaction-inert solvent and preferably in the presence of a suitable base.

c) reductively N-alkylating an intermediate of formula (IV) with a ketone or aldehyde of formula (VI),

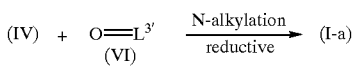

which represents a derivative of formula H—$L^3$ wherein two geminal hydrogen atoms are replaced by oxygen and $L^3$ is defined as in claim 1, in the presence of a reducing agent and optionally in the presence of a suitable catalyst;

d) condensing a pyridazinamine of formula (VII), wherein $R^1$, $R^2$, $R^3$, X, Alk, m and n are defined as in claim 1, with a phenol of formula (VIII)

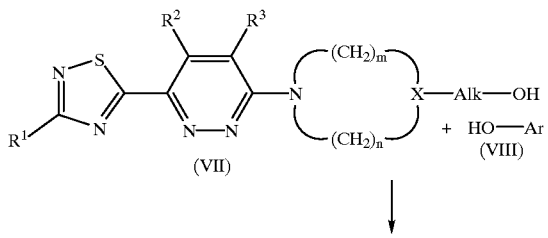

-continued

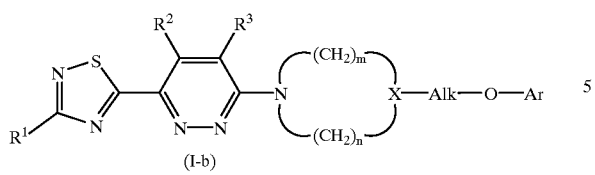
(I-b)

wherein Ar is defined as in claim 1, in a reaction-inert solvent;

e) O-alkylating a pyridazinamine derivative of formula (IX), wherein $R^1$, $R^2$, $R^3$, X, Alk, m and n are defined as in claim 1 and W is an appropriate leaving group, with a phenol of formula (VIII),

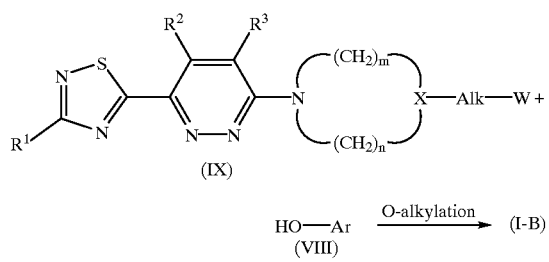

in a reaction-inert solvent and preferably in the presence of a suitable base;

f) reacting a ketone of formula (X)

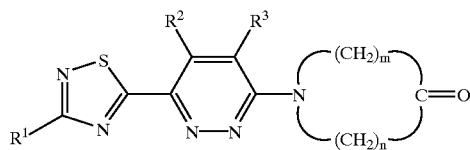

wherein $R^1$, $R^2$, $R^3$, m and n are defined as in claim 1, with an ylide of formula (XI)

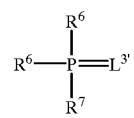
(XI)

wherein $R^6$ and $R^7$ are aryl or $C_{1-6}$alkyl, or $R^6$ is alkyloxy and $R^7$ is $O^-$, and $(R^6)_2R^7P=L^{3'}$, represents a derivative of formula $H-L^3$ wherein two geminal hydrogen atoms are replaced by $(R^6)_2R^7P=$, followed by reducing the thus obtained intermediate (XII)

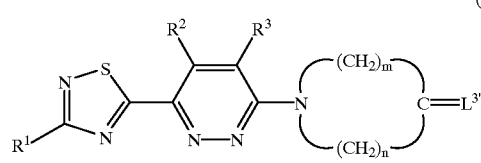
(XII)

in the presence of a suitable reducing agent in a reaction-inert solvent, to obtain a compound of formula

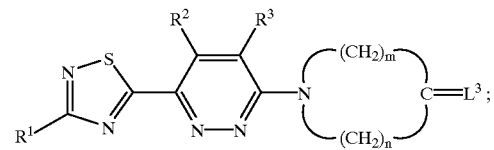
(I-c)

or, converting compounds of formula (I) into each other; and, if desired, converting compounds of formula (I) into a therapeutically active non-toxic acid addition salt by treatment with an acid, or conversely, converting the acid addition salt form into the free base by treatment with alkali; and, if desired, preparing stereochemically isomeric forms or N-oxide forms thereof.

10. A method of treating angiogenesis dependent disorders comprising administering to a host in need thereof an effective amount of a compound as claimed in claim 1.

* * * * *